United States Patent
AlJuaid et al.

(10) Patent No.: US 11,406,936 B2
(45) Date of Patent: Aug. 9, 2022

(54) $H_2S$ GAS SCRUBBING AND MONITORING SYSTEM FOR LABORATORY APPLICATIONS

(71) Applicant: SAUDI ARABIAN OIL COMPANY, Dhahran (SA)

(72) Inventors: Mohammed Thewaiban AlJuaid, Dammam (SA); Fahad Abdulla AlHamad, Dammam (SA); Finbarr Brian Healy, Dhahran (SA); Mike Ponstingl, Fenton, MO (US); Bandar Mohammed AlMosa, Dhahran (SA); Mohammed Saleh AlJawfi, Khobar (SA); Richard Nordman, Fenton, MO (US)

(73) Assignee: SAUDI ARABIAN OIL COMPANY, Dhahran (SA)

(*) Notice: Subject to any disclaimer, the term of this patent is extended or adjusted under 35 U.S.C. 154(b) by 0 days.

(21) Appl. No.: 16/927,493

(22) Filed: Jul. 13, 2020

(65) Prior Publication Data

US 2022/0008864 A1  Jan. 13, 2022

(51) Int. Cl.
*B01D 53/02* (2006.01)
*B01D 53/14* (2006.01)
(Continued)

(52) U.S. Cl.
CPC ......... *B01D 53/52* (2013.01); *B01D 53/0415* (2013.01); *B01D 53/1468* (2013.01);
(Continued)

(58) Field of Classification Search
CPC .............. B01D 53/52; B01D 53/0415; B01D 53/1468; B01D 53/18; B01D 2252/20415;
(Continued)

(56) References Cited

U.S. PATENT DOCUMENTS 4,380,586 A   4/1983  Saltzman
4,409,199 A * 10/1983  Blytas ................... C01B 17/165
                                               423/576.6
(Continued)

FOREIGN PATENT DOCUMENTS

CN   109569136 A   4/2019
DE   10242355 A1   7/2003
RU   2315297 C1    1/2008

OTHER PUBLICATIONS

Davidson et al., Measurement of Parts per Million Level Gaseous Concentration of Hydrogen Sulfide by Ultraviolet Spectroscopy using 1,1,1,5,5,5-Hexafluoropentan-2,4-dione as a Derivative by Reaction of Cu(hfac)(1,5-Cyclooctadiene), Apr. 10, 2009, Anal. Chem. 2009, 81, 9, 3669-3675 (Year: 2009).*

(Continued)

*Primary Examiner* — Frank M Lawrence, Jr.
(74) *Attorney, Agent, or Firm* — Osha Bergman Watanabe & Burton LLP

(57) ABSTRACT

A system for scrubbing and monitoring $H_2S$ includes: a sample inlet valve that controls an input stream of the hydrocarbon gas from the gas canister; a first scrubber that removes a first portion of $H_2S$ from the input stream and that outputs a first stream with less $H_2S$ than the input stream; a second scrubber that removes a second portion of $H_2S$ from the first stream and that outputs a second stream with less $H_2S$ than the first stream; a $H_2S$ converter that converts all remaining $H_2S$ in the second stream into a di-ketone and that outputs an output stream with a concentration of the di-ketone; an optical detector that measures the concentration of the di-ketone in the output stream; and a processor that determines a concentration of $H_2S$ in the second stream based on the concentration of the di-ketone in the output stream.

18 Claims, 11 Drawing Sheets

(51) Int. Cl.
  *B01D 53/52* (2006.01)
  *B01D 53/04* (2006.01)
  *B01D 53/18* (2006.01)
  *C07C 7/00* (2006.01)
  *C07C 7/11* (2006.01)
  *G01N 21/31* (2006.01)

(52) U.S. Cl.
  CPC .............. *B01D 53/18* (2013.01); *C07C 7/005* (2013.01); *C07C 7/11* (2013.01); *G01N 21/31* (2013.01); *B01D 2252/20415* (2013.01); *B01D 2252/20436* (2013.01); *B01D 2253/1124* (2013.01); *B01D 2256/24* (2013.01); *B01D 2257/304* (2013.01); *G01N 2201/061* (2013.01); *G01N 2201/062* (2013.01)

(58) Field of Classification Search
  CPC .. B01D 2252/20436; B01D 2253/1124; B01D 2256/24; B01D 2257/304; C07C 7/005; C07C 7/11; G01N 21/31; G01N 2201/061; G01N 2201/062
  USPC .......... 95/235; 96/121, 131, 132; 423/242.1, 423/243.01, 244.01, 244.06
  See application file for complete search history.

(56) References Cited

U.S. PATENT DOCUMENTS

| | | | |
|---|---|---|---|
| 4,934,256 A | | 6/1990 | Moss et al. |
| 5,674,463 A | * | 10/1997 | Dao .................. B01D 53/8606 |
| | | | 423/230 |
| 2007/0269357 A1 | | 11/2007 | Anderson et al. |
| 2009/0060808 A1 | | 3/2009 | Baum et al. |
| 2016/0061798 A1 | * | 3/2016 | Wapelhorst ......... H01J 49/0422 |
| | | | 73/23.2 |

OTHER PUBLICATIONS

Davidson, J. Michael et al., "Measurement of Parts per Million Level Gaseous Concentration of Hydrogen Sulfide by Ultraviolet Spectroscopy using 1,1,1,5,5,5-Hexafluoropentan-2,4-dione as a Derivative by Reaction of Cu(hfac)(1,5-Cyclooctadiene)", Analytical Chemistry, American Chemical Society, vol. 81, No. 9, May 2009, pp. 3669-3675 (7 pages).

Sadegh-Vaziri, Ramiar and Matthaus U. Babler, "Removal of Hydrogen Sulfide with Metal Oxides in Packed Bed Reactors—A Review from a Modeling Perspective with Practical Implications", Applied Sciences, MDPI, vol. 9, No. 5316, Dec. 2019, pp. 1-24 (24 pages).

Georgiadis, Amvrosios G. et al., "Removal of Hydrogen Sulfide From Various Industrial Gases: A Review of The Most Promising Adsorbing Materials", Catalysts, MDPI, vol. 10, No. 521, May 2020, pp. 1-36 (36 pages).

Adeniyi, Kayode I. et al., "High-Pressure Hydrogen Sulfide Experiments: How Did Our Safety Measures and Hazard Control Work during a Failure Event", Safety, MDPI, vol. 6, No. 15, Mar. 2020, pp. 1-12 (12 pages).

International Search Report issued in corresponding International Application No. PCT/US2020/045734, dated Dec. 16, 2020 (4 pages).

Written Opinion issued in corresponding International Application No. PCT/US2020/045734, dated Dec. 16, 2020 (7 pages).

* cited by examiner

US 11,406,936 B2

$H_2S$ GAS SCRUBBING AND MONITORING SYSTEM FOR LABORATORY APPLICATIONS

TECHNICAL FIELD

Embodiments described herein relate generally to systems and methods for scrubbing and monitoring hydrogen sulfide ($H_2S$).

BACKGROUND

Hydrocarbon samples from oil and gas wells are often transferred to a research laboratory from compositional analysis. The hydrocarbon samples are generally vented into a fume hood and out of the laboratory exhaust system when analysis is complete. However, some hydrocarbon samples contain toxic $H_2S$ gas that must be treated or removed prior to disposal of the hydrocarbon sample. The concentration of $H_2S$ in hydrocarbon samples generally varies between 0 and 45%.

SUMMARY

In one aspect, one or more embodiments disclosed herein relate to a system for scrubbing and monitoring $H_2S$ from a gas canister containing a hydrocarbon gas with $H_2S$. The system includes: a sample inlet valve that controls an input stream of the hydrocarbon gas from the gas canister; a first scrubber that removes a first portion of $H_2S$ from the input stream and that outputs a first stream with less $H_2S$ than the input stream; a second scrubber that removes a second portion of $H_2S$ from the first stream and that outputs a second stream with less $H_2S$ than the first stream; a $H_2S$ converter that converts all remaining $H_2S$ in the second stream into a di-ketone and that outputs an output stream with a concentration of the di-ketone; an optical detector that measures the concentration of the di-ketone in the output stream; and a processor that determines a concentration of $H_2S$ in the second stream based on the concentration of the di-ketone in the output stream.

In another aspect, one or more embodiments disclosed herein relate to a method for scrubbing and monitoring $H_2S$ from a gas canister containing a hydrocarbon gas with $H_2S$. The method includes: controlling an input stream of the hydrocarbon gas from the gas canister with a sample inlet valve; removing a first portion of $H_2S$ from the input stream with a first scrubber that outputs a first stream with less $H_2S$ that the input stream; removing a second portion of $H_2S$ from the first stream with a second scrubber that outputs a second stream with less $H_2S$ than the first stream; converting all remaining $H_2S$ in the second stream into a di-ketone with an $H_2S$ converter that outputs an output stream with a concentration of di-ketone; measuring the concentration of the di-ketone in the output stream with an optical detector; and determining a concentration of $H_2S$ in the second stream based on the concentration of the di-ketone in the output stream.

Other aspects and advantages will be apparent from the following description and the appended claims.

DETAILED DESCRIPTION

Figure 1:
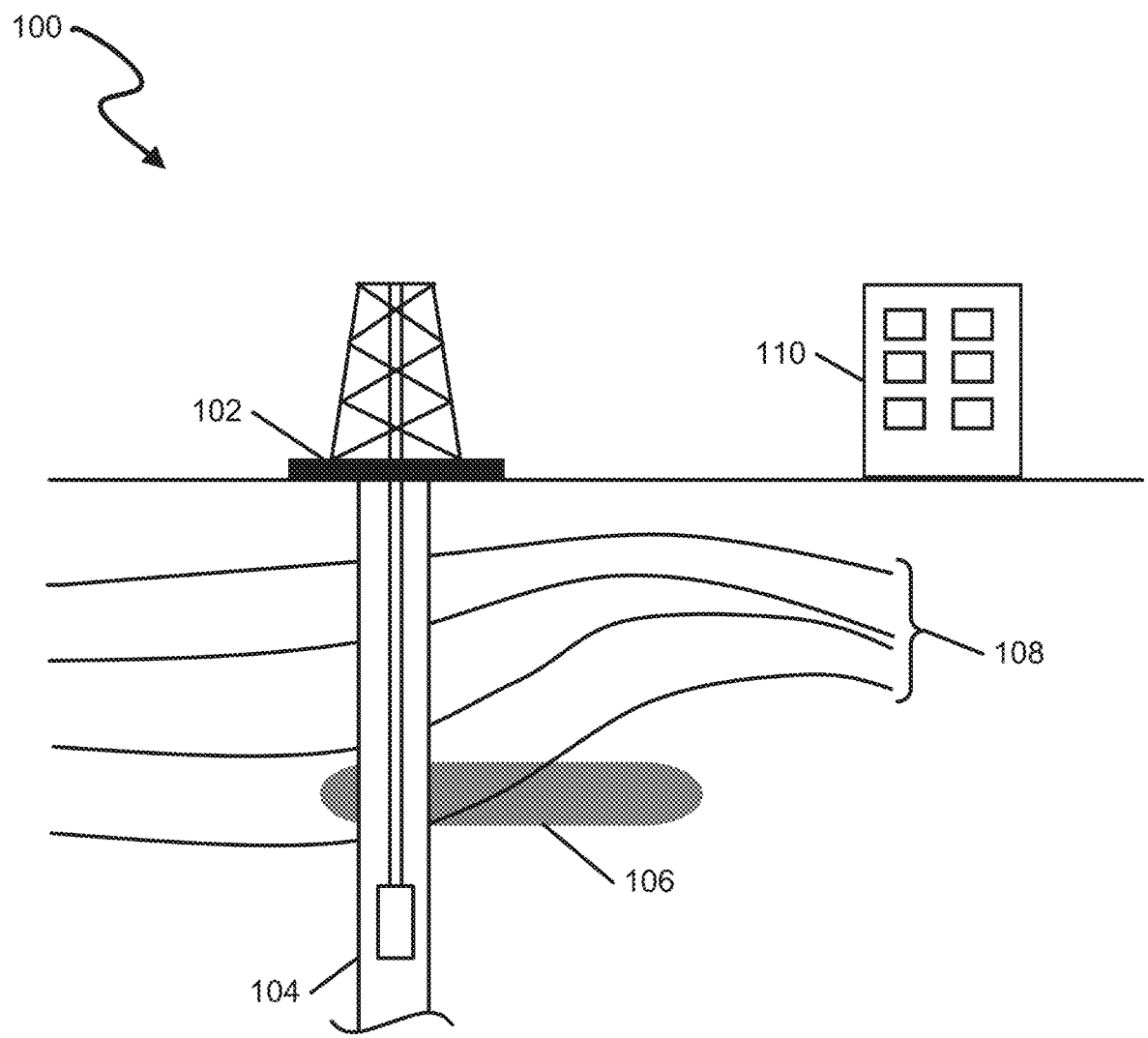
FIG. 1 shows a schematic of an oil and gas production facility.

Specific embodiments of the present disclosure will now be described in detail with reference to the accompanying figures. Like elements in the various figures are denoted by like reference numerals for consistency.

Numerous specific details are set forth in the following detailed description in order to provide a more thorough understanding of embodiments of the present disclosure. However, it will be apparent to one of ordinary skill in the art that the present disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create a particular ordering of the elements nor to limit any element to being only a single element unless expressly disclosed, such as by the use of the terms "before," "after," "single," and other such terminology. Rather the use of ordinal numbers is to distinguish between the elements. By way of an example, a first element is distinct from a second element, and the first element may encompass more than one element and succeed (or precede) the second element in an ordering of elements.

As shown in FIG. 1, an oil and gas production facility 100 may include an oil rig 102 and an oil well 104 that extract hydrocarbons 106 from a geological formation 108. Samples collected from the oil well 104 may include a variety of useful hydrocarbon fluids and gases that are analyzed in a research facility 110 to determine characteristics of the reservoir 108 and hydrocarbons 106. After completion of the analysis, the hydrocarbon samples can be disposed of by venting the hydrocarbon gas into the atmosphere.

In general, embodiments disclosed herein provide a system and a method for safe scrubbing and monitoring $H_2S$ to ensure safe levels of $H_2S$ removal from hydrocarbon gas samples in a laboratory environment. Specifically, embodiments disclosed herein improve the reliability of the hydrocarbon sample disposal process by accurately monitoring of the concentration of $H_2S$ by converting the remaining $H_2S$ in the scrubbed hydrocarbon sample into a di-ketone that is easier to optically detect (e.g., with an absorbance measurement) than $H_2S$. The di-ketone may be easier to detect because the absorptivity of the di-ketone is relatively higher than $H_2S$. In addition, the absorption peak of the di-ketone may be offset from the absorption peaks of other molecules in the hydrocarbon sample (e.g., aromatics, benzene, toluene, xylene, COS, $CS_2$, $SO_2$, mercaptans, Thiophene, Ethyl Methyl Disulfide, Diethyl Disulfide, light alkanes, fuel gases, and the like) that are likely to interfere with a direct absorbance measurement of $H_2S$. After the concentration of the di-ketone is measured, the concentration of $H_2S$ in the scrubbed gas may be determined based on the stoichiometry of the $H_2S$ to di-ketone conversion reaction. Because the di-ketone is easier to detect, the concentration of $H_2S$ can be accurately monitored at the low pressures of a scrubber system output pressures and without interference from other compounds in the gas stream.

Figure 2:
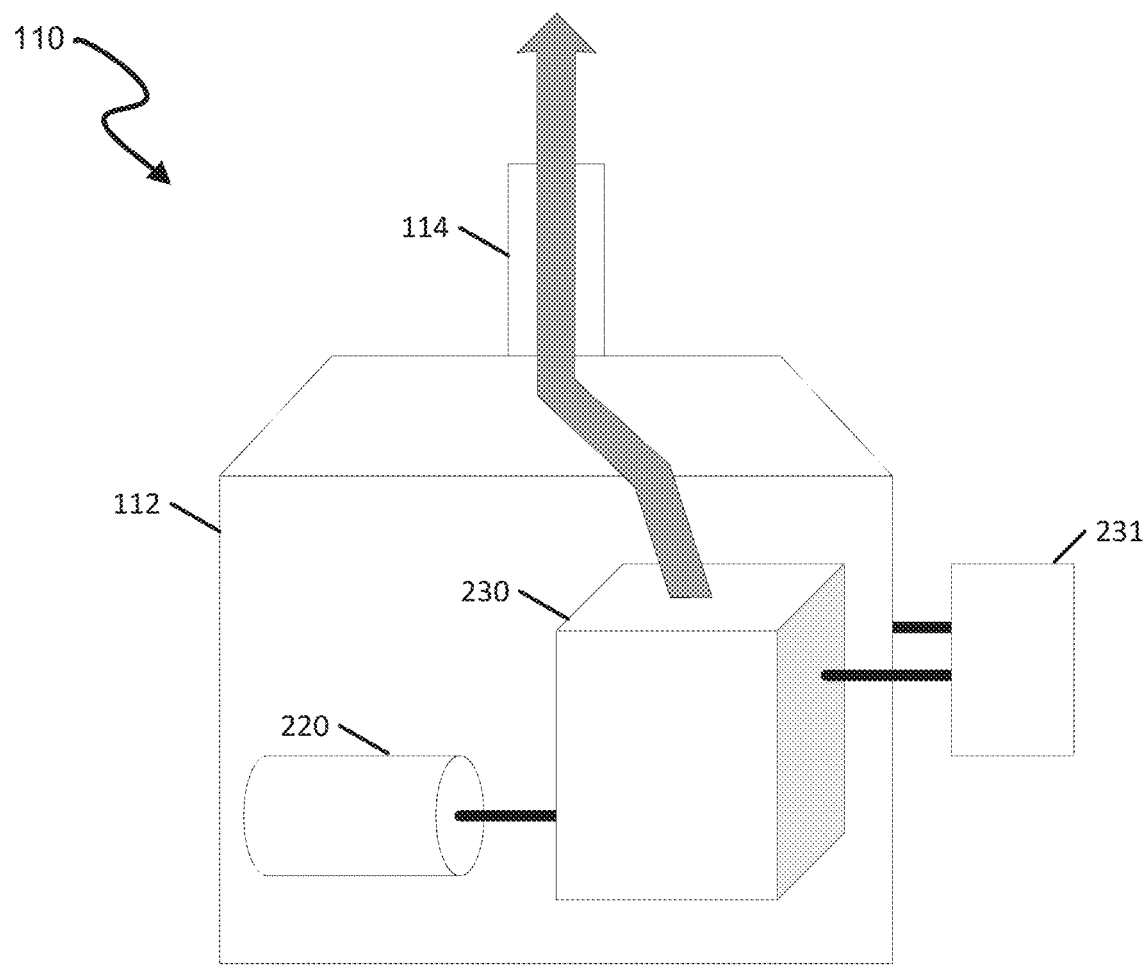
FIG. 2 shows a schematic of hydrocarbon sample disposal according to one or more embodiments.

As shown in FIG. 2, according to one or more embodiments, after completion of the testing on the hydrocarbon samples in the research facility 110, a gas canister 220 containing the hydrocarbon samples can be connected to a scrubber system 230 disposed in a fume hood 112 of the research facility 110. After the scrubber system 230 removes the $H_2S$, the fume hood 112 vents the scrubbed hydrocarbon sample through the exhaust system 114 of the research facility 110 and into the atmosphere. When the scrubber system 230 detects that the concentration of $H_2S$ in the scrubbed hydrocarbon sample exceeds a predetermined threshold, a controller 231 of the scrubber system halts the hydrocarbon disposal process to prevent venting of toxic $H_2S$ gas into the atmosphere (e.g., by sealing the gas canister 220, sealing the scrubber system 230, sealing the fume hood 112, sealing the exhaust system 114, or any combination thereof). The scrubber system 230 may be enclosed within an enclosure 230a to limit exposure of a user to the hydrocarbon gases. Accordingly, the controller 231 may be disposed outside of the enclosure 230a to allow the user to control and monitor the scrubber system 230 from safety.

A gas canister 220 containing a hydrocarbon gas sample with $H_2S$ is attached to the scrubber system 230. The scrubber system 230 may remove a maximum concentration of 50% $H_2S$ gas from the gas canister 220 within an 8-hour operation period. The gas canister 220 may be a 19 liter (5 gallon) field canister, which may fit within a standard laboratory walk-in fume hood, and also have the capacity to dispose of the high (up to 50%) $H_2S$ levels; however, depending on the size of the fume hood, volume of hydrocarbon gas and concentration of $H_2S$, another size of canister may be used. The operational capacity of the scrubber system 230 may depend on the concentration of $H_2S$ in the gas canister 220. For example, the components of the scrubber system may need to be recharged or replaced after scrubbing 19 liters of hydrocarbon gas with a 50% $H_2S$ concentration or after scrubbing 867 liters of hydrocarbon gas with a 2% $H_2S$ concentration. However, one of ordinary skill will appreciate that the maximum concentration removed and the operational period may be adjusted to any value by scaling the components of the scrubber system 230 accordingly (e.g., shorter operational periods or higher maximum concentrations may be achieved by expanding the capacity of the scrubber system 230).

Figure 3:
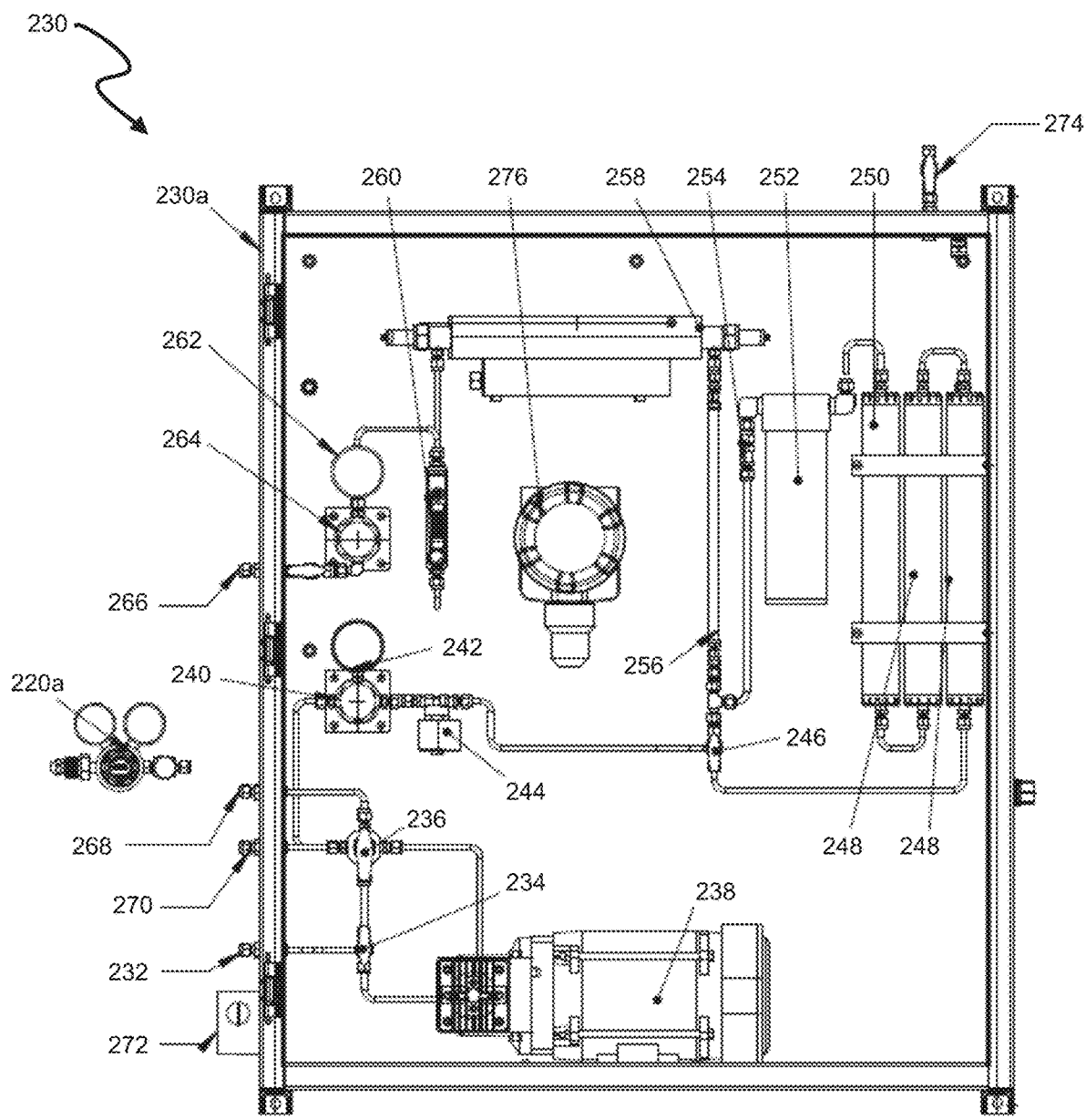
FIG. 3 shows a schematic of a system for $H_2S$ scrubbing and $H_2S$ monitoring according to one or more embodiments.

FIG. 3 shows a schematic of the scrubber system 230 for scrubbing and monitoring $H_2S$ according to one or more embodiments. The enclosure 230a of the scrubber system 230 may be a 304 stainless steel NEMA 4× style enclosure with dimensions, for example, of 700 mm by 1000 mm by 300 mm (or alternatively dimensions of 36 inches by 42 inches by 12 inches); however, it is understood that other sizing may be used depending on the size of the fume hood, for example. The enclosure 230a may further include one or more access doors to provide a user safe access to the various components of the scrubber system 230 discussed in detail below.

The gas canister 220 (shown in FIG. 2) may be connected to the enclosure 230a at a sample inlet valve 232. When open, the sample inlet valve 232 introduces the hydrocarbon gas into the scrubber system 230 as an input stream. The pressure of the input stream may be regulated by a canister regulator 220a (e.g., a two-stage pressure regulator with a 0-5000 psi first stage and a 0-100 psi second stage and a set point of 80 psi) attached to the gas canister 220 before the sample inlet valve 232. The canister regulator 220a prevents damage to the scrubber system due to over pressurization.

Within the enclosure 230a of the scrubber system 230, the input stream is further controlled by a first 3-way valve 234. The first 3-way valve 234 may be a SS-42GXS-4 ball valve (Swagelok), for example. When the first 3-way valve 234 is set to a first position A, the input stream is directly passed to a 5-way valve 236. Alternatively, when the first 3-way valve 234 is set to a second position B, the input stream may be passed to a sample pump 238 that extracts the hydrocarbon gas from the gas canister 220. The sample pump 238 may be a R252-FP-NA1 pump (Air Dimensions, Inc.), for example. The sample pump 238 may control (e.g., pressurize to 0-100 psi) the input stream when a pressure of the hydrocarbon gas in the gas canister 220 is lower than a pressure in the scrubber system 230 (i.e., when there is a dead volume within the gas canister 220). The sample pump 238 passes the pressurized input stream to the 5-way valve 236.

The 5-way valve 236, in addition to accepting inputs from the first 3-way valve 234 and the sample pump 238, may also accept inputs from a purge inlet valve 268 and span inlet valve 270 of the scrubber system 230, which are discussed in further detail below. The 5-way valve 236 may be a SS-43ZF2-GR ball valve (Swagelok), for example. The 5-way valve 236 passes the input stream to a first pressure regulator 240 and first pressure gauge 242.

The first pressure regulator 240 and first pressure gauge 242 may be controlled and monitored manually to regulate and monitor a pressure of the input stream. The first pressure regulator 240 may have a range of 0-100 psi with a set point of 60 psi. The first pressure gauge 242 may have a range of 0-100 psi.

An emergency shut-off valve 244 disposed after the first pressure regulator 240 may stop the scrubber system 230 by sealing the input stream from the rest of the scrubber system 230. The emergency shut-off valve 244 may be an EF8320A511 explosion proof solenoid valve (ASCO), for example, and may be controlled by the controller 231. The emergency shut-off valve 244 may include a bypass control that allows for high pressure in the scrubber system 230 during calibration, as discussed in further detail below. When the emergency shut-off valve 244 is open, the input stream passes to a second 3-way valve 246 (e.g., a SS-42GXS-4 ball valve (Swagelok)).

When the second 3-way valve 246 is set to a first position A, the input stream is passed directly to an $H_2S$ converter 256. The second 3-way valve 246 may include a locking mechanism to ensure the second 3-way valve 246 is locked in a second position B during operation of the scrubber system 230. When the second 3-way valve 246 is set to the second position B, the input stream is first passed through the first scrubber 248.

The first scrubber 248 removes a first portion of $H_2S$ from the input stream. The first scrubber 248 may comprise one or more dry canisters containing a first metal oxide (e.g., iron oxide) that adsorbs the first portion of $H_2S$ in the input stream. Each canister of the first scrubber 248 may be an interchangeable and/or disposable 2300 Series $H_2S$ Scrubber (Custom Sensors and Technology), for example. As shown in FIG. 3, the first scrubber 248 may comprise two dry duty canisters that are connected in series. However, as discussed with reference to FIG. 4A below, the first scrubber 248 may comprise two or more dry canisters connected in parallel to facilitate the exchange of canisters when a quality of the first metal oxide in one canister is depleted.

Alternatively, the first scrubber 248 may be a wet scrubber comprising a wet canister containing a triazine solution that reacts with the first portion of $H_2S$ in the input stream, as discussed with reference to FIG. 4B below.

Regardless of the use of metal oxide or triazine to remove the first portion of $H_2S$ from the input stream, the first scrubber 248 outputs a first stream with less $H_2S$ than the input stream. For example, in one or more embodiments, the first scrubber 248 may remove greater than 99% of the $H_2S$ in the input stream. The first stream is passed from the first scrubber 248 to the second scrubber 250.

The second scrubber 250 removes a second portion of $H_2S$ from the first stream. The second scrubber 250 may comprise one or more canisters of a second metal oxide (e.g., copper oxide) that adsorbs the second portion of $H_2S$ in the first stream. The copper oxide canister may be an interchangeable and/or disposable 2300 Series $H_2S$ Scrubber (Custom Sensors and Technology), for example. As shown in FIG. 3, the second scrubber 250 may comprise a single canister connected in series with the first scrubber 248. As discussed with reference to FIG. 4 below, the second scrubber 250 may comprise two or more canisters connected in parallel to facilitate the exchange of canisters when the quality of the second metal oxide is depleted. The second scrubber 250 outputs a second stream with less $H_2S$ than the first stream. For example, in one or more embodiments, there is less than 1 ppm $H_2S$ in the second stream that is output from the second scrubber 250.

The second stream may be passed from the second scrubber 250 through a particulate filter 252 and a check valve 254 before being directed to an $H_2S$ converter 256. The particulate filter 252 may be a 3C-060-504-P stainless steel flow separator filter (Reading Technologies, Inc.), for example. The check valve 254 may be 1 psi poppet check valve (e.g., SS-4C-NE-1 valve (Swagelok)), for example.

The second stream is passed through the $H_2S$ converter 256 that reacts with any remaining $H_2S$ in the second stream and converts the remaining $H_2S$ into a di-ketone. The $H_2S$ converter 256 may be a 2200 Series $H_2S$ Converter (Custom Sensors and Technologies), for example. The $H_2S$ converter 256 may be a canister comprising cycloocta-1,5-diene-1,1,1,5,5,5-hexafluoropentan-2,4-dionatocopper(I) (Cu(hfac)(COD)) that reacts with $H_2S$ to yield 1,1,1,5,5,5-hexafluoropentan-2,4-dione (Hhfac). However, the canister may comprise any appropriate converter species that reacts with $H_2S$ to form a di-ketone with higher molar absorptivity than $H_2S$ (e.g., Hhfac has approximately 12 times the molar absorptivity of $H_2S$). The $H_2S$ converter 256 outputs an output stream with no remaining $H_2S$ and a concentration of di-ketone that is proportional to the concentration of $H_2S$ in the second stream. The output stream is passed from the $H_2S$ converter 256 to the optical detector 258.

Figure 5:
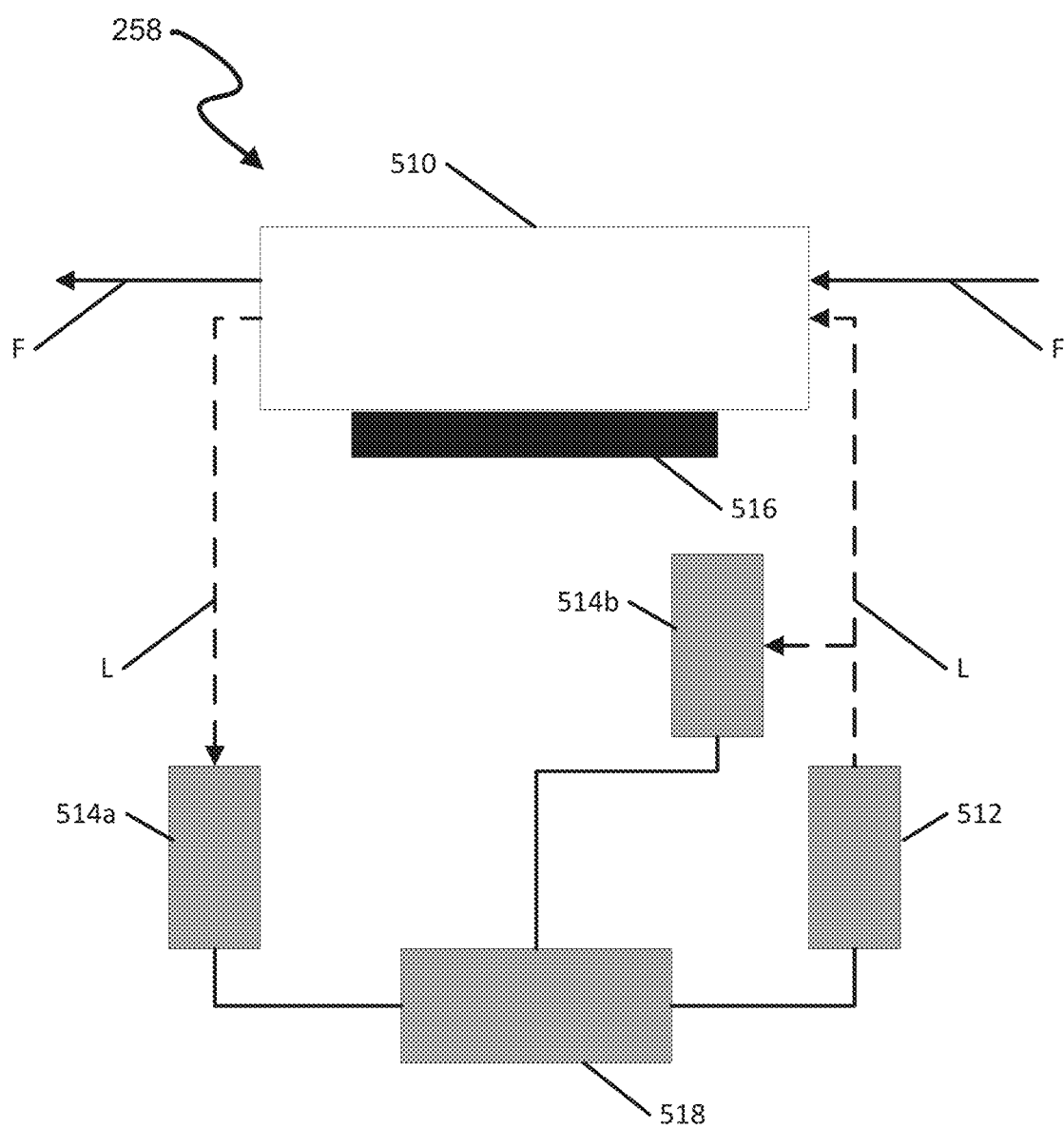
FIG. 5 shows an optical detector according to one or more embodiments.

The optical detector 258, discussed in further detail with respect to FIG. 5, detects a concentration of the di-ketone in the output stream. Because the absorptivity of the di-ketone may be centered at a larger wavelength than the absorptivity of $H_2S$, the optical detector 258 may detect the di-ketone with improved selectivity (i.e., reduced interference) from other molecules in the output stream (e.g., aromatics, benzene, toluene, xylene, COS, $CS_2$, $SO_2$, organics, light alkanes, fuel gases, and the like). The optical detector 258 may be controlled by the controller 231 that determines and outputs the concentration of $H_2S$ in the second stream based on the concentration of the di-ketone in the output stream. The output stream may be passed from the optical detector 258 to a flow meter 260.

The flow meter 260 measures a flow rate of the scrubber system 230 and may be connected to the controller 231. The flow meter 260 may be a VAF-G1-01M-2-0 variable area flow meter (Swagelok) with a range of 0.5-5 liters per hour and a set point of 2.4 liters per hour, for example.

Based on the flow rate of the scrubber system 230, the controller 231 may calculate, estimate, or track the quality of the first and second scrubbers 248, 250 and/or the $H_2S$ converter 256. For example, the quality of the first and second scrubbers 248, 250 and/or the $H_2S$ converter 256 may be inversely related to the flow rate or duty cycle of the of the scrubber system 230. The output stream may pass from flow meter 260 to a second pressure gauge 262 and a second pressure regulator 264.

The second pressure gauge 262 and the second pressure regulator 264 may be controlled manually to regulate and monitor a pressure and flow rate of the output stream. The second pressure gauge 262 may be a PGI-63B-8G15-LAOX pressure gauge (Swagelok) with a range of 0-15 psi and a set point of 5 psi, for example. The second pressure regulator 264 may be a KBP1C0A4A5A20000 stainless steel back pressure regulator (Swagelok) with a range of 0-10 psi, for example. The output stream is passed from the second pressure regulator 264 to the sample outlet 266.

The sample outlet 266 vents the output stream from the scrubber system 230. Referring back to FIG. 2, in one or more embodiments, the output stream is vented into the fume hood 112 and exhaust system 114 of the research facility 110. Thus, after the scrubber system 230 has removed the toxic $H_2S$ component from the hydrocarbon sample contained in the gas canister 220, the remainder of the hydrocarbon sample can be safely vented into the atmosphere through the exhaust system 114.

As discussed above, the purge inlet valve 268 is connected to the 5-way valve 236 to flush the scrubber system 230. A purge gas (e.g., an inert gas such as $N_2$) may be injected into the purge inlet 268 to remove any contaminants in the scrubber system 230. Similarly, the span inlet 270 is connected as an input to the 5-way valve 236 and may be used to calibrate the scrubber system 230, as discussed in further detail below.

In one or more embodiments, the enclosure 230a of the scrubber system 230 includes an enclosure purge inlet valve 272 and an enclosure purge vent valve 274. A purge gas (e.g., an inert gas such as $N_2$) may be injected into the enclosure purge inlet 272 to remove any contaminants that may have leaked into the enclosure 230a from the scrubber system 230.

In one or more embodiments, the enclosure 230a of the scrubber system 230 further includes an enclosure $H_2S$ monitor 276 that directly measures a concentration of $H_2S$ in the enclosure 230a. The enclosure $H_2S$ monitor 276 may warn the user of any potential $H_2S$ inside the enclosure (e.g., from a leak due to improper assembly of the scrubber system 230) via the controller 231. For example, the enclosure $H_2S$ monitor 276 may be a Honeywell® Sensepoint XCD RTD gas sensor with 0-100 ppm sensitivity and an alarm threshold of 20 ppm, for example.

Figure 4A:
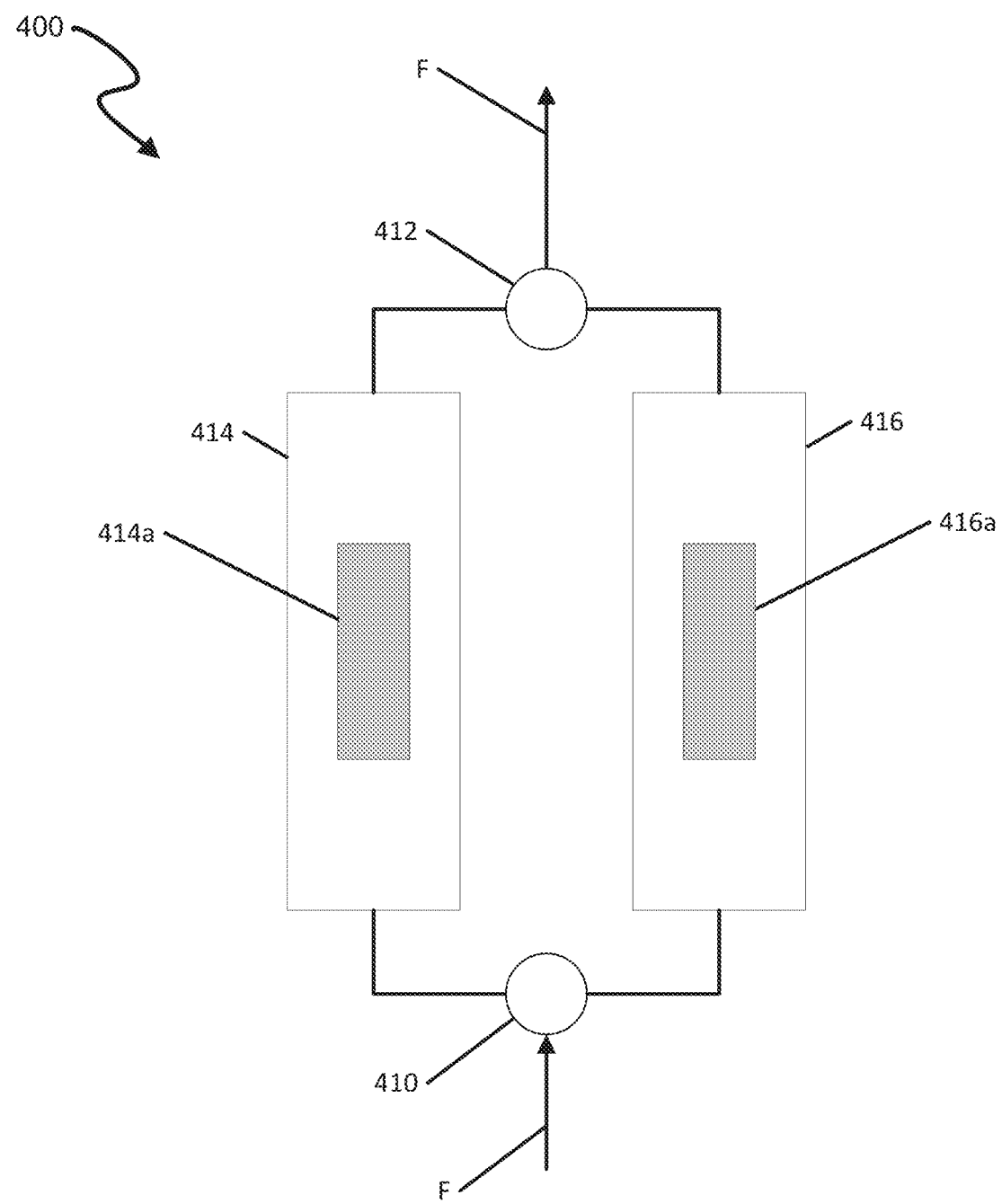
FIG. 4A shows a dry scrubber according to one or more embodiments.

FIG. 4A shows a dry scrubber stage 400 according to one or more embodiments. As discussed above, one or more of the first and/or second scrubbers 248, 250 of the scrubber system 230 may be configured in a parallel configuration, exemplified by the dry scrubber stage 400, to facilitate the exchange of canisters when the quality of the metal oxide adsorbate is depleted. The dry scrubber stage 400 may comprise a first selection valve 410 and a second selection valve 412 that initially direct a flow F through a duty canister 414 while one or more standby canisters 416 are sealed off from flow F.

As the scrubber system 230 operates, the metal oxide in the duty canister 414 becomes saturated and gradually reduces the quality of the duty canister 414. This may be indicated by a color change of the metal oxide that may be viewed through a duty canister sight glass 414a installed in a surface of the duty canister 414. Alternatively, the controller 231 may indicate when the duty canister 414 should be replaced based on usage. For example, optical detector 258 and controller 231 may monitor $H_2S$ gas readings to determine when duty canister 414 should be replaced.

When the duty canister 414 is depleted, the first and second selection valves 410, 412 are manipulated to divert flow from the depleted duty canister 414 to the standby canister 416. Thus, the depleted duty canister 414 may be removed and replaced by the user without interrupting operation of the scrubber system 230. Accordingly, the standby canister 416 may then be monitored through the standby canister sight glass 416a or the controller 231 that measures usage. For example, optical detector 258 and controller 231 may monitor $H_2S$ gas readings to determine when standby canister 416 should be replaced.

Figure 4B:
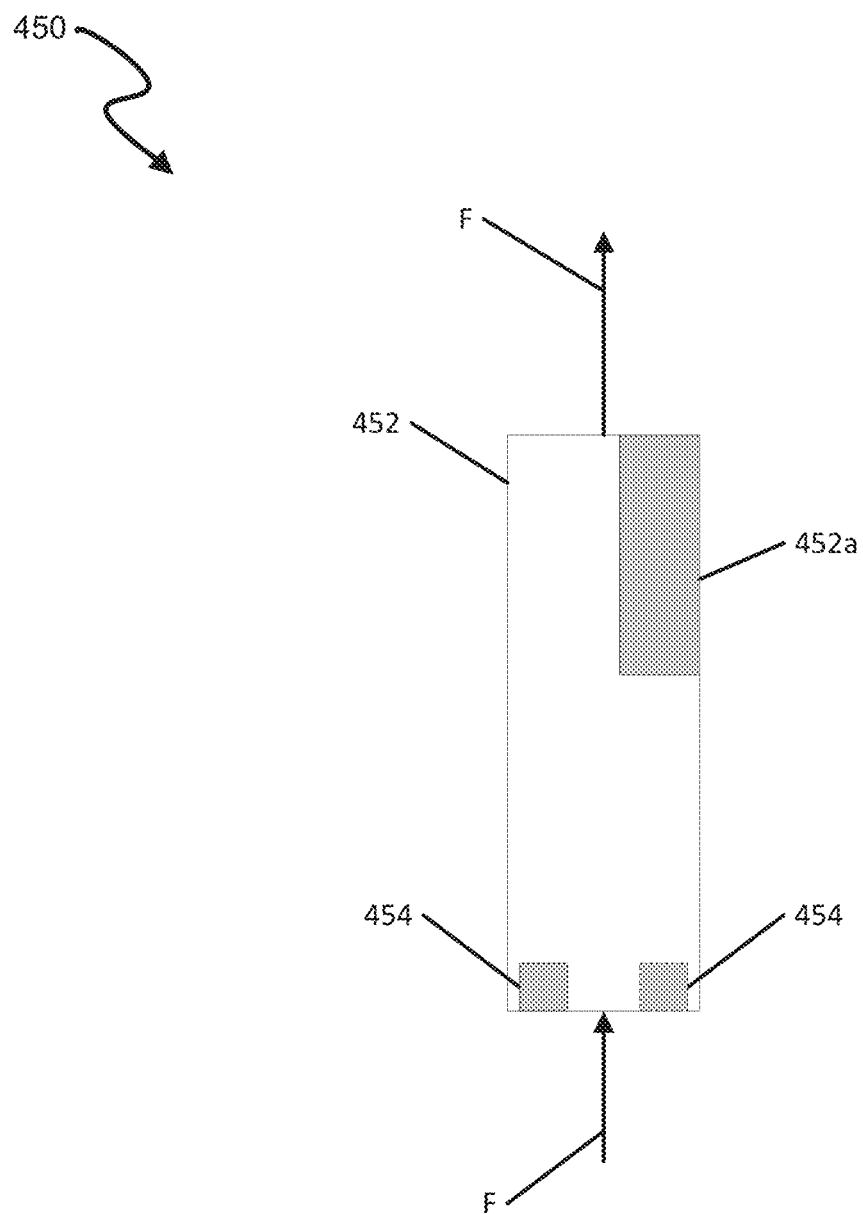
FIG. 4B shows a wet scrubber according to one or more embodiments.

FIG. 4B shows a wet scrubber 450 according to one or more embodiments. As discussed above, the first scrubber 248 may be a wet scrubber 450 that includes a triazine canister 452 instead of a dry canister 414. As the input stream moves along flow F through the triazine canister 452, a triazine solution contained in the triazine canister 452 reacts with the $H_2S$ to remove the first portion of $H_2S$ from the input stream. The triazine canister may accept a maximum input stream pressure of 100 psi.

As the scrubber system 230 operates, the triazine solution in the triazine canister 452 is gradually depleted. This may be detected by a triazine sensor 452a installed in the triazine canister 452. Alternatively, the controller 231 may indicate when the triazine canister 452 should be replenished based on usage. For example, optical detector 258 and controller 231 may monitor $H_2S$ gas readings to determine when triazine canister 452 should be replaced.

When the quality of the triazine canister 452 is reduced, the triazine solution may be drained and replaced through a triazine fill/drain port 454 installed in the triazine canister 452. In one or more embodiments, the triazine canister 452 may include two triazine fill/drain ports 454 to allow the triazine solution to be filled and drained at the same time (i.e., without interrupting the scrubber system 230).

FIG. 5 shows an optical detector 258 according to one or more embodiments. As discussed above, the optical detector 258 detects a concentration of the di-ketone in the output stream. The optical detector 258 may be configured to perform a single source absorbance measurement (e.g., Custom Sensors and Technology PX2+ Photometric Transmitter). The optical detector 258 may be controlled by the controller 231.

The optical detector 258 includes a flow cell 510 through which a gas (e.g., the output stream from the $H_2S$ converter 256) flows, as flow F, and is measured. The optical detector further includes a light source 512 that emits light L of a measurement wavelength. For example, the light source 512 may be a xenon flash lamp that emits a broad range of wavelengths (e.g., 200-1200 nm) that contains the desired measurement wavelength or a light emitting diode (LED) that emits the measurement wavelength. The measurement wavelength may simultaneously be tuned to overlap an absorption peak of the di-ketone and avoid an absorption peak of $H_2S$ or other molecules in the output stream (e.g., aromatics, benzene, toluene, xylene, COS, $CS_2$, $SO_2$, organics, light alkanes, fuel gases, and the like). In one or more embodiments, the measurement wavelength may include 270 nm or any appropriate wavelength that improves selectivity of the di-ketone and reduces interference from molecules other than the di-ketone.

The emitted light is passed through the flow cell 510 and detected by a first detector 514a that measures the light absorbed by the output stream in the flow cell 510. In one or more embodiments, the optical detector 258 further comprises a second detector 514b that directly measures a reference intensity of light directly from the light source 512 before it is passed through the flow cell 510. The optical detector 258 may further comprise any necessary optical components to filter, redirect, or focus the light between the light source 512 and the detectors 514a, 514b (e.g., a lens, a beam splitter, a fiber optic waveguide, a mirror, a wavelength filter, a spatial filter, a beam block).

In one or more embodiments, the optical detector 258 may further comprise a flow cell heater 516 that maintains the gas in the flow cell 510 at a constant predetermined temperature (e.g., 140° F.) to improve accuracy of the absorbance measurement and avoid fluctuations caused by a temperature sensitivity of the molecules in the gas volume.

Based on the intensity measured by the one or more detectors 514a, 514b, an absorbance of the gas is calculated at the measurement wavelength. Based on the absorbance measurement and the geometry of the flow cell 510, a concentration of the di-ketone may be calculated (e.g., based on Beer's Law) by a processor 518 of the optical detector 258 and/or by the controller 231.

Upon measuring the concentration of the di-ketone in the output stream, the controller 231 may determine the concentration of $H_2S$ in the second stream based on the concentration of the di-ketone in the output stream and stoichiometry of the conversion reaction in the $H_2S$ converter 258. If the $H_2S$ concentration exceeds a predetermined threshold (e.g., an excess of $H_2S$ is still present after scrubbing), the controller 231 may seal the gas canister 220, seal the enclosure 230a of the scrubbing system 230, seal the fume hood 210, or any combination thereof to prevent the output stream or the contents of the gas canister 220 from being released from the scrubber system 230. The controller 231 may output the concentration of $H_2S$ to the user with an output device, as discussed in further detail with respect to FIG. 6.

Figure 6:
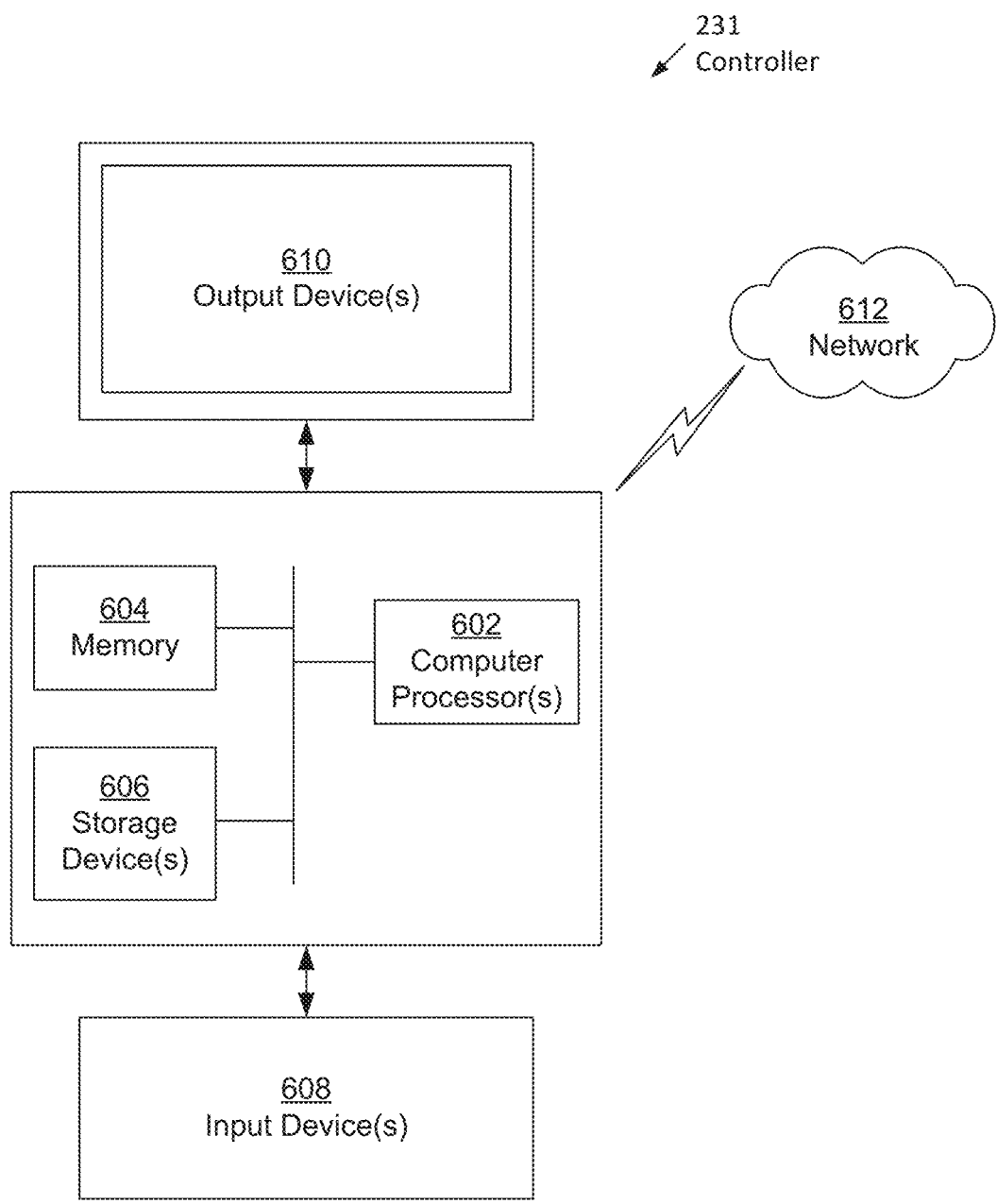
FIG. 6 shows a controller according to one or more embodiments.

FIG. 6 shows a schematic of a controller 231 according to one or more embodiments. As discussed above, in one or more embodiments, the controller 231 may monitor and control various components of the scrubber system 300 (e.g., any valve, any pressure regulator, the sample pump 238, the optical detector 258, or the like), perform calculations based on the optical detector 258, and exchange information and/or data with the scrubber system 300 or a user. The controller 231 may be implemented on virtually any type of computing system, regardless of the platform being used. For example, the computing system may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments disclosed herein. For example, as shown in FIG. 6 the controller 231 may include one or more computer processor(s) 602, associated memory 604 (e.g., random access memory (RAM), cache memory, flash memory), one or more storage device(s) 606 (e.g., a hard disk, an optical drive such as a compact disk (CD) drive or digital versatile disk (DVD) drive, a flash memory stick), and numerous other elements and functionalities. The computer processor(s) 602 may be an integrated circuit for processing instructions. For example, the computer processor(s) may be one or more cores, or micro-cores of a processor.

The controller 231 may also include one or more input device(s) 608, such as an input signal connection with one or more components of the scrubber system 230 that are contained within the enclosure 230a (e.g., the pressure gauge 242, optical detector 258, flow meter 260, second pressure gauge 262, or the like), camera, imager, touchscreen, keyboard, mouse, microphone, touchpad, electronic pen, or any other type of input device. Further, the controller 231 may include one or more output device(s) 610, such as a control signal connection with one or more components of the scrubber system 230 that are contained within the enclosure 230a (e.g., a valve, the sample pump 238, a regulator, the optical detector 258, or the like), a screen (e.g., a liquid crystal display (LCD), an audio and/or visual alarm, a plasma display, touchscreen, cathode ray tube (CRT) monitor, or other display device), a printer, external storage, or any other output device. One or more of the output device(s) may be the same or different from the input device(s). The controller 231 may be connected to a network 612 (e.g., a local area network (LAN), a wide area network (WAN) such as the Internet, mobile network, or any other type of network) via a network interface connection (not shown). The input and output device(s) may be locally or remotely (e.g., via the network 612) connected to the computer processor(s) 602, memory 604, and storage device(s) 606. Many different types of computing systems exist, and the aforementioned input and output device(s) 608, 610 may take other forms.

Further, one or more elements of the controller 231 may be located at a remote location and be connected to the other elements over a network 612. Further, one or more embodiments may be implemented on a distributed system having a plurality of nodes, where each portion of the embodiment may be located on a different node within the distributed system. In one embodiment, the node corresponds to a distinct computing device. In other embodiments, the node may correspond to a computer processor with associated physical memory. In yet other embodiments, the node may correspond to a computer processor or micro-core of a computer processor with shared memory and/or resources.

Figure 7A:
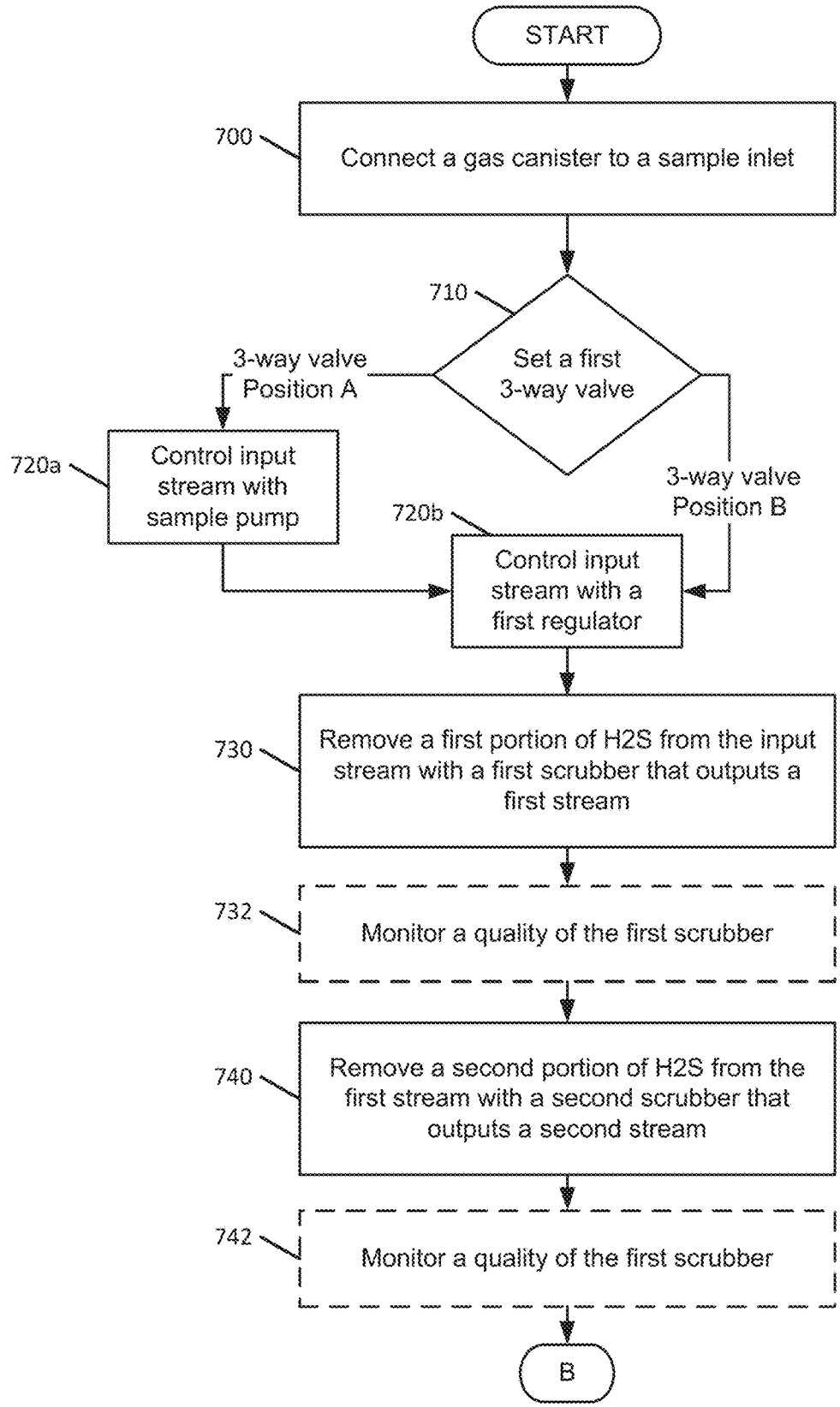
FIGS. 7A and 7B show a flowchart of a method of scrubbing $H_2S$ and monitoring $H_2S$ according to one or more embodiments.
Figure 7B:
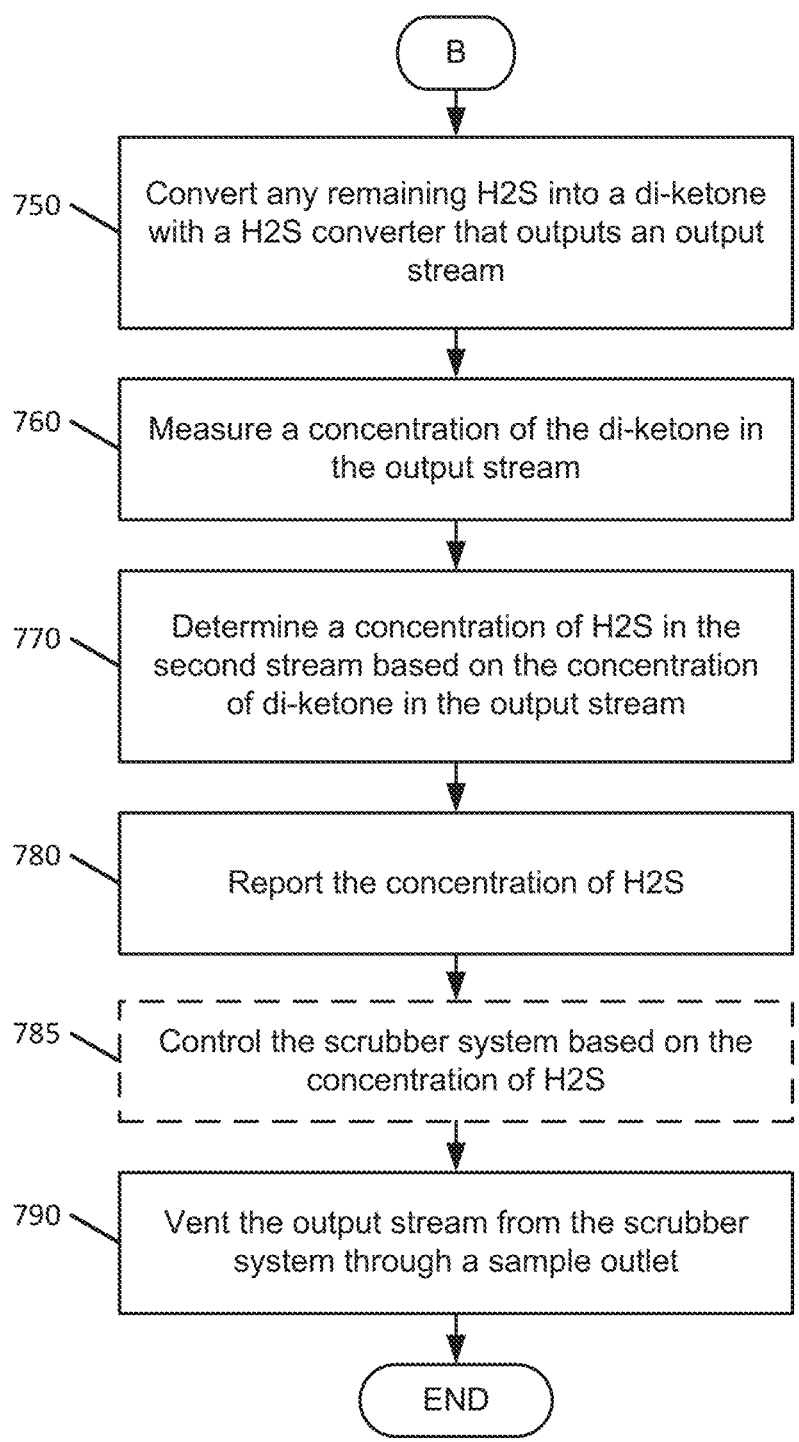
Figure 8A:
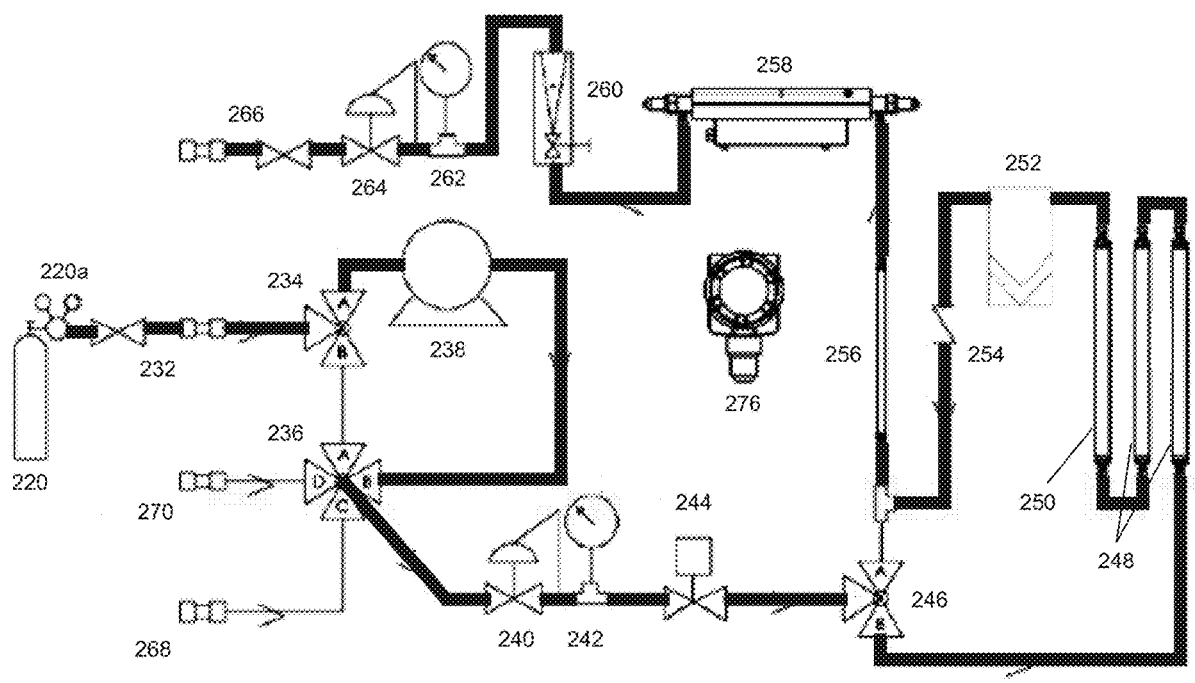
FIGS. 8A and 8B show schematics of a method of scrubbing $H_2S$ and monitoring $H_2S$ according to one or more embodiments.
Figure 8B:
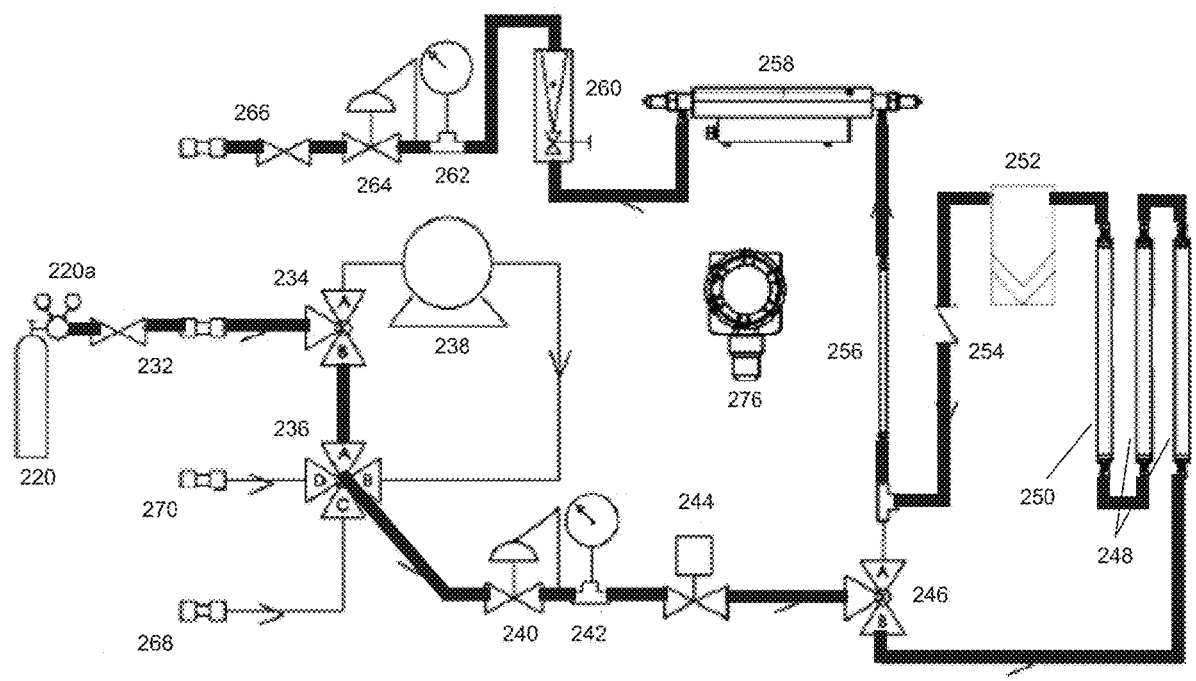

FIGS. 7A and 7B shows a flowchart of a method of scrubbing $H_2S$ and monitoring $H_2S$ according to one or more embodiments. FIGS. 8A and 8B show schematics of the system corresponding to the method shown in FIGS. 7A and 7B. The flowchart and schematics depict a method for scrubbing and monitoring $H_2S$ that may be performed using the scrubber system 230 described above in reference to FIGS. 2-6. In one or more embodiments, one or more of the steps shown in FIGS. 7A, 7B, 8A, and 8B may be combined, omitted, repeated, and/or performed in a different order than the order shown in FIGS. 7A, 7B, 8A, and 8B. Accordingly, the scope of the present disclosure should not be considered limited to the specific arrangement of steps shown in FIGS. 7A, 7B, 8A, and 8B.

At 700, a gas canister 220 is connected to a sample inlet valve 232 of a scrubbing system 230 that includes at least a first scrubber 248, a second scrubber 250, a $H_2S$ converter 256, and an optical detector 258. The gas canister 220 may be a 19 liter (5 gallon) field canister that needs to be scrubbed within an 8 hour period. However, the present disclosure is not limited to these values and other canister volumes or time periods may be used. The gas canister 220 may contain a hydrocarbon sample with $H_2S$. A concentration of $H_2S$ in the gas canister 220 may be equal to or less than 50%, however higher concentrations may be permitted if the scrubbing system 230 is scaled accordingly (e.g., adding additional first scrubbers 248 with adequate fume hood space).

In one or more embodiments, the sample inlet valve 232 is mounted in the side of an enclosure 230a that encloses the first scrubber 248, the second scrubber 250, the $H_2S$ converter 256, and the optical detector 258. The enclosure 230a may be disposed inside of a walk-in laboratory fume hood 112 that safely exhausts scrubbed gas through an exhaust system 114. However, the system may be scaled to any appropriate size to accommodate large or smaller gas canister volumes or $H_2S$ concentrations and may be applied to environments outside of a research laboratory.

At 710, a first 3-way valve 234 is set to either a first position A or a second position B, as shown in FIGS. 8A and 8B respectively.

At 720, an input stream of the hydrocarbon gas from the gas canister 220 is controlled. The input stream may be controlled by a canister regulator 220a or a valve of the sample inlet 232.

As shown in FIG. 8A, when the first 3-way valve 234 is set to the first position A at 710, the first 3-way valve 234 connects the gas canister 220 to a sample pump 238. At 720a, the input stream may be further controlled by the sample pump 238 that extracts the hydrocarbon gas from the gas canister 220 when the pressure within the gas canister 220 is less than a pressure in the scrubber system 230. The input stream is then passed, by a 5-way valve 236, to a first pressure regulator 240 regulates the pressurized input stream.

As shown in FIG. 8B, when the first 3-way valve 234 is set to the second position B at 710, the first 3-way valve 234 connects the gas canister 220, by way of the 5-way valve 236, to the first pressure regulator 240. At 720b, the input stream may be further controlled by the first pressure regulator 240 that regulates the input stream.

At 730, a first portion of $H_2S$ is removed from the input stream by a first scrubber 248. The first scrubber 248 may include one or more dry canisters of iron oxide that adsorbs the $H_2S$ to remove the first portion of $H_2S$ from the input stream. Alternatively, the first scrubber 248 may include a wet canister of a triazine solution that reacts with the input stream to remove the first portion of $H_2S$. The first scrubber 248 outputs a first stream that has less $H_2S$ than the input stream. For example, the first stream may have less than 1% concentration of $H_2S$.

At 732, the quality of the first scrubber 248 may be monitored. In one or more embodiments where the first scrubber 248 includes a first canister containing an iron oxide, a quality of the iron oxide may be monitored by a color change of the iron oxide that is visible through a sight glass disposed in the first canister. In one or more embodiments where the first scrubber 248 includes a triazine canister containing a triazine solution, a quality of the triazine solution may be monitored by a triazine sensor installed in the triazine canister.

At 740, a second portion of $H_2S$ is removed from the first stream by a second scrubber 250. The second scrubber 250 may include one or more canisters of copper oxide that adsorbs the $H_2S$ to remove the second portion of $H_2S$ from the first stream. The second scrubber 250 outputs a second stream that has less $H_2S$ than the first stream. For example, the second stream may have virtually 0% concentration of $H_2S$.

At 742, the quality of the second scrubber 250 may be monitored. In one or more embodiments where the second scrubber 250 includes a second canister containing a copper oxide, a quality of the copper oxide may be monitored by a color change of the copper oxide that is visible through a sight glass disposed in the second canister.

At 750, any remaining $H_2S$ in the second stream is converted into a di-ketone by a $H_2S$ converter 256. The $H_2S$ converter 256 may be a canister containing cycloocta-1,5-diene-1,1,1,5,5,5-hexafluoropentan-2,4-dione (Hhfac) that reacts rapidly and quantitatively at ppm levels with any remaining $H_2S$ in the second stream. However, other compounds or molecules may be used in the $H_2S$ converter 256 to convert the remaining $H_2S$ in the second stream into a di-ketone. In one or more embodiments, the $H_2S$ converter 256 is specific to reacting with $H_2S$ and can be used in the presence of $N_2$, $H_2$, CO, COS, $CS_2$, $SO_2$, moist air, $CH_3OH$, $C_2H_4$, $C_6H_6$, light alkanes including fuel gases, aromatics, Mercaptans, DMS and DMDS, Thiophene, Ethyl Methyl Disulfide, Diethyl Disulfide, and the like. The $H_2S$ converter 256 outputs an output stream containing a concentration of the di-ketone.

At 760, the concentration of the di-ketone in the output stream is measured by an optical detector 258. In one or more embodiments, the optical detector 258 performs a single source absorbance measurement on the output stream as it flows through a flow cell 510. The flow cell 510 may be heated to a constant 131° F. However, one of ordinary skill will appreciate that the flow cell 510 may be adjusted to another appropriate temperature to prepare the output stream for measurement. The output stream flowing through the flow cell 510 may be regulated by the various valves and regulators the scrubber system 230 to maintain a constant pressure and flow rate for accurate monitoring of the concentration of the di-ketone.

The optical detector 258 may emit light of a measurement wavelength through the flow cell 510 that passes the output stream. The optical detector 258 then detects the light emitted through the flow cell 510 to calculate the absorbance of di-ketone in the output stream. The measurement wavelength may be chosen to simultaneously overlap an absorption peak of the di-ketone and avoid an absorption peak of $H_2S$ or other molecules in the output stream (e.g., aromatics, benzene, toluene, xylene, COS, $CS_2$, $SO_2$, organics, light alkanes, fuel gases, and the like). For example, the measurement wavelength may be 270 nm or any appropriate wavelength that improves selectivity of the di-ketone and reduces interference from molecules other than the di-ketone.

At 770, a concentration of $H_2S$ in the second stream is determined based on the concentration of the di-ketone in the output stream. The concentration of $H_2S$ may be determined based on the stoichiometry of the conversion reaction in the $H_2S$ converter 258.

At 780, the scrubber system 230 reports the concentration of $H_2S$ to a user with an output device of a controller 231 (e.g., a display, an indicator, an alarm, or the like).

At 785, the controller 231 may control the scrubber system 230 based on the concentration of $H_2S$. For example, if the concentration of $H_2S$ exceeds a predetermined threshold, the controller 231 may control one or more of the input stream, first stream, second stream, and/or the output stream. In one or more embodiments, the controller 231 may stop the scrubber system 230 by closing one or more valves (e.g., an emergency shut-off valve 244). The controller 231 may seal the gas canister 220, seal the enclosure 230a of the scrubbing system 230, seal the fume hood 210, or any combination thereof to prevent the output stream or the contents of the gas canister 220 from being released from the scrubber system 230. In one or more embodiments, the controller 231 may reduce the flow rate or pressure of the scrubber system 230 by controlling one or more regulators (e.g., the first pressure regulator 240) to regulate the scrubbing efficiency.

At 790, the output stream is vented from the scrubber system 230 through a sample outlet valve 266. In one or more embodiments, the sample outlet valve 266 is disposed on the enclosure 230a and vents the output stream into the walk-in fume hood 112 that encloses the enclosure 230a and the gas canister 220.

As discussed above, in one or more embodiments, the 5-way valve 236 may be used to calibrate the system by connecting the purge inlet valve 268 and the span inlet 270 to the scrubber system 230.

To re-zero the scrubber system 230 (i.e., perform a zero calibration), a purge gas (i.e., a zero gas) is supplied through purge inlet valve 268, 5-way valve 236 is set to position C, and second 3-way valve 246 is set to position A. After allowing time for the purge gas to fill the scrubber system 230 (e.g., 3 minute to fill), a stable pressure (e.g., 5 psi) and a stable flow rate (e.g., 2.4 L/hr) are established before the concentration of the purge gas is recorded and stored by the controller 231.

To record another calibration point for the scrubber system 230, a span gas is supplied through span inlet valve 270, 5-way valve 236 is set to position D, and second 3-way valve 246 is set to position A. After allowing time for the span gas to fill the scrubber system 230 (e.g., 3 minute to fill), a stable pressure (e.g., 5 psi) and a stable flow rate (e.g., 2.4 L/hr) are established before the concentration of the span gas is recorded and stored by the controller 231.

Software instructions in the form of computer readable program code to perform embodiments of the present disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments disclosed herein.

One or more of the embodiments disclosed herein may have one or more of the following advantages and improvements over conventional scrubbing techniques: improving detection of $H_2S$ in a scrubber system by selectively converting $H_2S$ to a di-ketone that can be optically detected with less interference (compared to $H_2S$) from other molecules present in the scrubbing system. Embodiments of the scrubber system and the method for scrubbing and monitoring $H_2S$ disclosed herein ensure the reliability of the laboratory hydrocarbon disposal processes by monitoring the concentration of residual H$_2$S in the scrubbed hydrocarbon sample with less interference from other molecules in the hydrocarbon sample.

Although the disclosure has been described with respect to only a limited number of embodiments, those skilled in the art, having benefit of this disclosure, will appreciate that various other embodiments may be devised without departing from the scope of the present disclosure. Accordingly, the scope of the disclosure should be limited only by the attached claims.

What is claimed:

1. A system for scrubbing and monitoring H$_2$S from a gas canister containing a hydrocarbon gas with H$_2$S, the system comprising:
   a sample inlet valve that controls an input stream of the hydrocarbon gas from the gas canister;
   a first scrubber that removes a first portion of H$_2$S from the input stream and that outputs a first stream with less H$_2$S than the input stream;
   a second scrubber that removes a second portion of H$_2$S from the first stream and that outputs a second stream with less H$_2$S than the first stream;
   a H$_2$S converter that converts all remaining H$_2$S in the second stream into a di-ketone and that outputs an output stream with a concentration of the di-ketone;
   an optical detector that measures the concentration of the di-ketone in the output stream;
   a processor that determines a concentration of H$_2$S in the second stream based on the concentration of the di-ketone in the output stream;
   an enclosure that includes the sample inlet valve and that encloses the first scrubber, the second scrubber, the H$_2$S converter, and the optical detector; and
   a walk-in fume hood that encloses the enclosure, wherein the output stream is vented from the enclosure into the walk-in fume hood.

2. The system according to claim 1, wherein
   the first scrubber includes an iron oxide that removes the first portion of H$_2$S from the input stream, and
   the second scrubber includes a copper oxide that removes the second portion of H$_2$S from the first stream.

3. The system according to claim 2, wherein
   the iron oxide is contained in a first canister with a sight glass that visually indicates a quality of the iron oxide, and
   the copper oxide is contained in a second canister with a sight glass that visually indicates a quality of the copper oxide.

4. A system for scrubbing and monitoring H$_2$S from a gas canister containing a hydrocarbon gas with H$_2$S, the system comprising:
   a sample inlet valve that controls an input stream of the hydrocarbon gas from the gas canister;
   a first scrubber that removes a first portion of H$_2$S from the input stream and that outputs a first stream with less H$_2$S than the input stream;
   a second scrubber that removes a second portion of H$_2$S from the first stream and that outputs a second stream with less H$_2$S than the first stream;
   a H$_2$S converter that converts all remaining H$_2$S in the second stream into a di-ketone and that outputs an output stream with a concentration of the di-ketone;
   an optical detector that measures the concentration of the di-ketone in the output stream;
   a processor that determines a concentration of H$_2$S in the second stream based on the concentration of the di-ketone in the output stream, wherein
   the first scrubber includes a triazine solution that removes the first portion of H$_2$S from the input stream, and
   the second scrubber includes a copper oxide that removes the second portion of H$_2$S from the first stream.

5. The system according to claim 4, wherein
   the triazine is contained in a first canister with a triazine sensor that monitors a quality of the triazine solution, and
   the copper oxide is contained in a second canister with a sight glass that visually indicates a quality of the copper oxide.

6. The system according to claim 1, wherein
   the optical detector comprises:
   a flow cell that the output stream flows through;
   a light source that emits light of a measurement wavelength through the flow cell; and
   a detector that detects the light emitted through the flow cell.

7. The system according to claim 6, wherein the measurement wavelength is 270 nm.

8. The system according to claim 6, wherein the flow cell comprises a heater that heats the flow cell to a constant 131° F. during operation.

9. The system according to claim 1, further comprising:
   a sample pump disposed after the sample inlet valve and before the first scrubber, wherein
   the sample pump extracts the hydrocarbon gas from the gas canister and controls the input stream when a pressure in the gas canister is lower than a pressure in the system.

10. A method for scrubbing and monitoring H$_2$S from a gas canister containing a hydrocarbon gas with H$_2$S, the method comprising:
    controlling an input stream of the hydrocarbon gas from the gas canister with a sample inlet valve;
    removing a first portion of H$_2$S from the input stream with a first scrubber that outputs a first stream with less H$_2$S that the input stream;
    removing a second portion of H$_2$S from the first stream with a second scrubber that outputs a second stream with less H$_2$S than the first stream;
    converting all remaining H$_2$S in the second stream into a di-ketone with an H$_2$S converter that outputs an output stream with a concentration of di-ketone;
    measuring the concentration of the di-ketone in the output stream with an optical detector; and
    determining a concentration of H$_2$S in the second stream based on the concentration of the di-ketone in the output stream;
    connecting the gas canister to an enclosure that includes a sample inlet valve and that encloses the first scrubber, the second scrubber, the H$_2$S converter, the optical detector; and
    venting the output stream from the enclosure into a walk-in fume hood that encloses the enclosure.

11. The method according to claim 10, wherein
    the first portion of H$_2$S is removed from the input stream by an iron oxide in the first scrubber, and
    the second portion of H$_2$S is removed from the first stream by a copper oxide in the second scrubber.

12. The method according to claim 11, further comprising:
    monitoring a quality of the iron oxide in the first scrubber; and
    monitoring a quality of the copper oxide in the second scrubber, wherein the iron oxide is contained in a first canister with a sight glass that visually indicates the quality of the iron oxide, and the copper oxide is contained in a second canister with a sight glass that visually indicates the quality of the copper oxide.

13. The method according to claim 10, wherein the first portion of $H_2S$ is removed from the input stream by a triazine solution in the first scrubber, and the second portion of $H_2S$ is removed from the first stream by a copper oxide in the second scrubber.

14. The method according to claim 13, further comprising monitoring a quality of the triazine solution in the first scrubber; and monitoring a quality of the copper oxide in the second scrubber, wherein the triazine solution is contained in a first canister with a triazine sensor that indicates the quality of the triazine solution, and the copper oxide is contained in a second canister with a sight glass that visually indicates the quality of the copper oxide.

15. The method according to claim 10, wherein detecting the concentration of the di-ketone in the output stream comprises:

flowing the output stream through a flow cell;

emitting light of a measurement wavelength through the flow cell while the output stream passes through the flow cell; and detecting the light emitted through the flow cell.

16. The method according to claim 15, wherein the measurement wavelength is 270 nm.

17. The method according to claim 15, wherein detecting the concentration of the di-ketone in the output stream further comprises heating the flow cell to a constant 131° F. during operation.

18. The method according to claim 10, wherein a sample pump that extracts the hydrocarbon gas from the gas canister is disposed after the sample inlet valve and before the first scrubber, and when a pressure in the gas canister is lower than a pressure in the system, controlling the input stream is performed by the sample pump.

* * * * *